United States Patent
Hiller et al.

(10) Patent No.: US 11,736,414 B2
(45) Date of Patent: Aug. 22, 2023

(54) APPARATUS WITH SERVICE INTERFACE AND METHOD FOR SERVICING THE APPARATUS

(71) Applicant: Erbe Elektromedizin GmbH, Tuebingen (DE)

(72) Inventors: Juergen Hiller, Dettingen (DE); Marc Kegreiss, Rottenburg (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 244 days.

(21) Appl. No.: 16/913,794

(22) Filed: Jun. 26, 2020

(65) Prior Publication Data
US 2020/0412668 A1  Dec. 31, 2020

(30) Foreign Application Priority Data
Jun. 27, 2019 (EP) .................... 19182969

(51) Int. Cl.
*H04L 49/40* (2022.01)
*G06F 13/12* (2006.01)
(Continued)

(52) U.S. Cl.
CPC ............ *H04L 49/40* (2013.01); *G06F 13/128* (2013.01); *G06Q 10/20* (2013.01); *G16H 40/63* (2018.01);
(Continued)

(58) Field of Classification Search
CPC ......... A47L 11/29; A61B 18/02; A61B 18/14; A61B 18/16; A61B 18/1206;
(Continued)

(56) References Cited

U.S. PATENT DOCUMENTS 7,338,443 B1 * 3/2008 Tucker .................. G16H 40/20
128/920
7,881,462 B2 * 2/2011 Hazani ................. H01R 13/719
379/413.04
(Continued)

FOREIGN PATENT DOCUMENTS

CN  104375473 A  2/2015
CN  108027901 A  5/2018
(Continued)

OTHER PUBLICATIONS

Extended European Search Report dated Dec. 13, 2019, in corresponding European Application No. 19182969.6, with machine English translation (11 pages).
(Continued)

*Primary Examiner* — Stephen R Burgdorf
(74) *Attorney, Agent, or Firm* — Fitch, Even, Tabin & Flannery LLP

(57) ABSTRACT

An apparatus comprising a socket insert that is arranged in a receptacle of the apparatus. The socket insert is connected to an operating medium connector. In the receptacle a data interface is covered by the socket insert and inaccessible from outside. To obtain access to the apparatus software or data, the socket insert can be replaced by a service insert that covers the operating medium output but contacts the data plug. The service insert allows communication with the apparatus control to input or output data and/or programs. The arrangement of the service interface covered by socket inserts provides an effective means for access control to the service interface. It impedes or avoids non-authorized access to the interface and damages for persons and material that otherwise could occur due to the missing disruptive discharge proof potential separation between the service inter-
(Continued)

face and particularly the power section of the apparatus control.

13 Claims, 4 Drawing Sheets

(51) Int. Cl.
  *G06Q 10/20* (2023.01)
  *H04L 49/00* (2022.01)
  *G16H 40/63* (2018.01)
(52) U.S. Cl.
  CPC ......... *H04L 49/30* (2013.01); *A61M 2209/00* (2013.01)
(58) Field of Classification Search
  CPC .......... A61B 2018/00172; A61B 2018/00577; A61B 2018/00589; A61B 2018/00601; A61B 2217/005; A61B 2560/045; A61B 2560/0475; A61M 2209/00; G01R 11/04; G01R 31/007; G05B 19/042; G06F 13/128; G06F 1/163; G06F 1/1632; G06F 1/266; G06Q 10/20; G07F 19/20; G16H 40/40; G16H 40/63; H01R 13/46; H01R 13/516; H01R 13/518; H01R 13/625; H01R 13/633; H01R 13/639; H01R 13/641; H01R 13/665; H01R 13/6691; H01R 13/707; H01R 13/74; H01R 13/743; H01R 24/60; H01R 31/06; H01R 35/02; H01R 2201/12; H04B 3/54; H04L 49/30; H04L 49/40
  USPC ...................................................... 340/572.1
  See application file for complete search history.

(56) References Cited

U.S. PATENT DOCUMENTS

| | | |
|---|---|---|
| 9,666,974 B2 | 5/2017 | Bopp |
| 10,309,873 B2 | 6/2019 | Jagiella et al. |
| 10,522,250 B2 | 12/2019 | Spohn et al. |
| 2002/0172001 A1* | 11/2002 | Homer .................... G06F 1/169 361/679.02 |
| 2003/0080630 A1 | 5/2003 | Liu |
| 2004/0214138 A1* | 10/2004 | Senn ..................... A61C 19/004 433/141 |
| 2005/0063116 A1 | 3/2005 | Rotheroe |
| 2006/0094276 A1* | 5/2006 | Till ....................... H01R 13/639 439/327 |
| 2007/0123065 A1 | 5/2007 | Rosenfeldt et al. |
| 2007/0141869 A1* | 6/2007 | McNeely ............... A47C 31/00 439/76.1 |
| 2007/0155349 A1* | 7/2007 | Nelson ............. H02J 13/00006 455/128 |
| 2008/0054073 A1* | 3/2008 | Charles .................. A61B 90/90 235/385 |
| 2008/0165476 A1* | 7/2008 | McCoy ................ H05K 5/0017 361/728 |
| 2012/0004649 A1 | 1/2012 | Schnitzler |
| 2012/0260012 A1 | 10/2012 | Gao-Saari et al. |
| 2015/0046125 A1 | 2/2015 | Jagiella et al. |
| 2015/0229083 A1 | 8/2015 | Bopp |
| 2016/0172808 A1* | 6/2016 | Lauby ................ H01R 13/6691 348/730 |
| 2016/0321467 A1 | 11/2016 | Keber et al. |
| 2017/0276702 A1* | 9/2017 | Freer .................. G01R 1/07378 |
| 2021/0250553 A1* | 8/2021 | Naber, Jr. ............. B60R 25/302 |

FOREIGN PATENT DOCUMENTS

| | | | | |
|---|---|---|---|---|
| EP | 1566864 A1 | | 8/2005 | |
| EP | 2904982 A1 | | 8/2015 | |
| ES | 2207323 T3 | | 5/2004 | |
| GB | 2595695 A | * | 12/2021 | .......... H01R 13/514 |
| RU | 2203008 C2 | | 4/2003 | |

OTHER PUBLICATIONS

Chinese First Office Action dated Aug. 24, 2021, in corresponding Chinese Application No. 202010587537.8, with English translation (14 pages).
Federal Institute of Industrial Property (FIPS), Russian Office Action with Search Report in corresponding Patent Application No. 2020120053/28(034035), dated May 18, 2023, 16 pages.

* cited by examiner

APPARATUS WITH SERVICE INTERFACE AND METHOD FOR SERVICING THE APPARATUS

RELATED APPLICATION(S)

This application claims the benefit of European Patent Application No. 19182969.6, filed Jun. 27, 2019, the contents of which are incorporated herein by reference as if fully rewritten herein.

TECHNICAL FIELD

The invention refers to an apparatus with service interface and a method for servicing the apparatus, particularly by ensuring an access control to a service interface.

BACKGROUND

For operation of medical instruments, particularly cryo-instruments, electrosurgical instruments and other instruments to be used during surgery on human and animal patients, apparatus are in use that are configured to supply the respective instruments with the needed operating media. Operating media can be media in form of a substance or energy. Operating media can be liquids, gases, vacuum, electrical voltages, electrical currents, visible or non-visible light. The operating media can carry and transport power and/or information. Examples for operating media are liquids or gases, like e.g. water, NaCl solution, argon, nitrogen, carbon dioxide, oxygen, aerosols or the like. The operating medium can be supplied to the instrument or can be drained off from the instrument (vacuum), e.g. for fume suction. The operating medium can be light, e.g. laser light that is supplied to the instrument in order to create an effect on biological tissue. It can also be light for surgery area illumination that is supplied to the instrument. Also light received by the instrument can be conducted to the apparatus. If the operating medium is electrical current, it can be direct current, alternating current, radio frequency alternating current that serves, e.g. for coagulation, thermal fusion, ablation, dissection or for creating other effects. The apparatus can be configured to provide and/or receive one or more of the named operating media. Both are comprised by the term "supply".

Such apparatus are in principle known from the prior art. For example, EP 2 904 982 A1 discloses an apparatus for this purpose with a housing closed at all sides that comprises receptacle at its front for socket inserts. Each socket insert ends flush at the front side with the apparatus front side and thus forms a portion of the front surface of the apparatus with view of a user. The socket insert comprises electrical connections (sockets) for connection of a surgical instrument. The socket insert is locked in the receptacle by means of releasable locking means and connected with the apparatus by means of a plug connection at the side facing away from the front side.

Such apparatus usually contain controls or other electrical circuits that can be parameterized and/or are program-controlled and/or gain and store data during operation and/or operate based on stored data. For service and maintenance purposes it is necessary to allow service technicians access to the electrical circuits, i.e. to their parameters and/or programs. For this typically a service interface is present that, however, must be electrically separated from the power section of the apparatus in order to exclude damages for persons and material also in case of clueless handling.

Starting therefrom it is an object of the invention to provide an apparatus for supply of medical instruments that comprises a service interface, wherein however with simple measures the damage of users shall be excluded.

SUMMARY

According to the inventive concept, the inventive apparatus comprises a service interface in form of a data plug that is arranged in the receptacle of a socket insert such that the service interface is covered by the socket insert in case the apparatus is provided ready for use and thus is not accessible for the user. For the service technician, who needs access to the data plug and thus to the apparatus control, the socket insert is removable from the receptacle. Typically the socket insert is locked by a locking means in the receptacle. The locking means can be configured such that it is releasable by means of a tool. For example, the locking means can comprise a release pin that can be axially moved in a hole that is accessible from the front side of the socket insert in order to release the locking means.

After removal of the socket insert from the receptacle, the service interface is accessible that can be configured, for example, as data plug (male or female). If the service interface is, for example, a standardized plug, such as a USB-plug or the like, now a respective cable can be connected to it and thus a connection can be established to an external device, e.g. a laptop. The data plug is covered by the socket insert and preferably not connected with it, but independent, if the socket insert is arranged in the receptacle. To guarantee this the socket insert or each other service interface can be configured such that it does not contain any connections connectable with the data plug.

At the limiting wall of the receptacle opposite the front side, i.e. at its back side, the operating medium output and the service interface, e.g. in the form of the data plug, are arranged. The operating medium output and the data plug are preferably arranged in a sideward distance from each other that allows a safe electrical insulation between the operating medium output and the data plug. The data plug and the operating medium output are thus spatially separated. Due to the spatial separation and the covering by the socket insert, electrical potential separation measures for the data plug can be omitted. This decreases the constructive effort and required space that otherwise would have to be provided for a safe high-voltage-resistant separation in the data line leading away from the data plug.

Typically a service insert is assigned to the apparatus that can be held and carried by the service technician. The service insert comprises an outer contour that allows the insertion of the service insert into the receptacle. The service insert comprises a housing that comprises a counterpart at an end face matching the service interface, e.g. a data plug (female or male) that is adapted to the data plug of the apparatus. The data plug is arranged at a location of the end face such that it engages the data plug of the apparatus during insertion into the receptacle and establishes a correct electrical connection.

The service insert typically comprises no connection for the operating medium output of the apparatus, such that the service insert is disconnected from the operating medium output of the apparatus and indeed also if the service insert is inserted into the receptacle.

The service insert can be configured exclusively passive by that it comprises a socket, e.g. a USB-socket, at a section of its housing extending out of the receptacle during use or simply at its front side. Other sockets, as e.g. two or multiple pole sockets, network sockets or the like can be provided in addition or as an alternative. One or more of such sockets form a communication interface to which other data processing devices, i.e. a computer, a laptop, a notebook, a tablet, a smartphone or the like can be connected.

Alternatively, the interface for communication with another computer can also be configured as network interface or as radio connection. For this the service insert can comprise a radio module, e.g. a Bluetooth module or a WLAN module that is configured for communication with respective remote stations, e.g. in form of a computer, a laptop, a notebook, a tablet, a smartphone or the like.

In addition or as an alternative, it is possible that the service insert contains own storage means and/or own data processing means that can be operated or activated by manual operating means or via a communication interface from another electronic device, such as for example a mobile device (mobile phone, tablet, laptop, notebook, etc.). The storage means can be configured to exchange data or programs with the control of the apparatus directly or via relaying of a computer accommodated in the service insert.

The preferred method for servicing of an apparatus comprises the removal of the socket insert from the receptacle, the insertion of the service insert in the receptacle, the activation of the service insert, the removal of the service insert from the receptacle and the reinsertion of the socket insert in the receptacle.

The insertion of the service insert in the receptacle comprises the coupling of the data plugs of the apparatus and the service insert. The activation of the service insert comprises the release of the data exchange between the service insert and the apparatus control or the data exchange between a data processing device (computer, laptop, notebook, tablet, smartphone) connected to the service insert and the apparatus control via the service insert. It is possible that the data exchange only comprises the transfer of data from the service insert to the apparatus control. It is also possible that the data exchange only comprises the transfer of data from the apparatus control to the service insert. It is further also possible that the data exchange comprises the data transfer in both directions indicated above.

The exchanged data can comprise or can be exclusively application programs. The exchanged data can be operating data or operating parameters of the apparatus or also measurement values collected by the apparatus that are provided on a storage of the apparatus or a storage provided in the service insert. In addition or as an alternative, the data can be transmitted via the data interface mentioned above to an external device, such as for example a computer device provided to the service technician, such as a mobile phone, a tablet, a laptop, a notebook or the like.

BRIEF DESCRIPTION OF THE DRAWINGS

Details of an exemplary embodiment of the invention are apparent from the drawings, the dependent claims or the description referring to the drawings. The drawings show:

DETAILED DESCRIPTION

Figure 1:
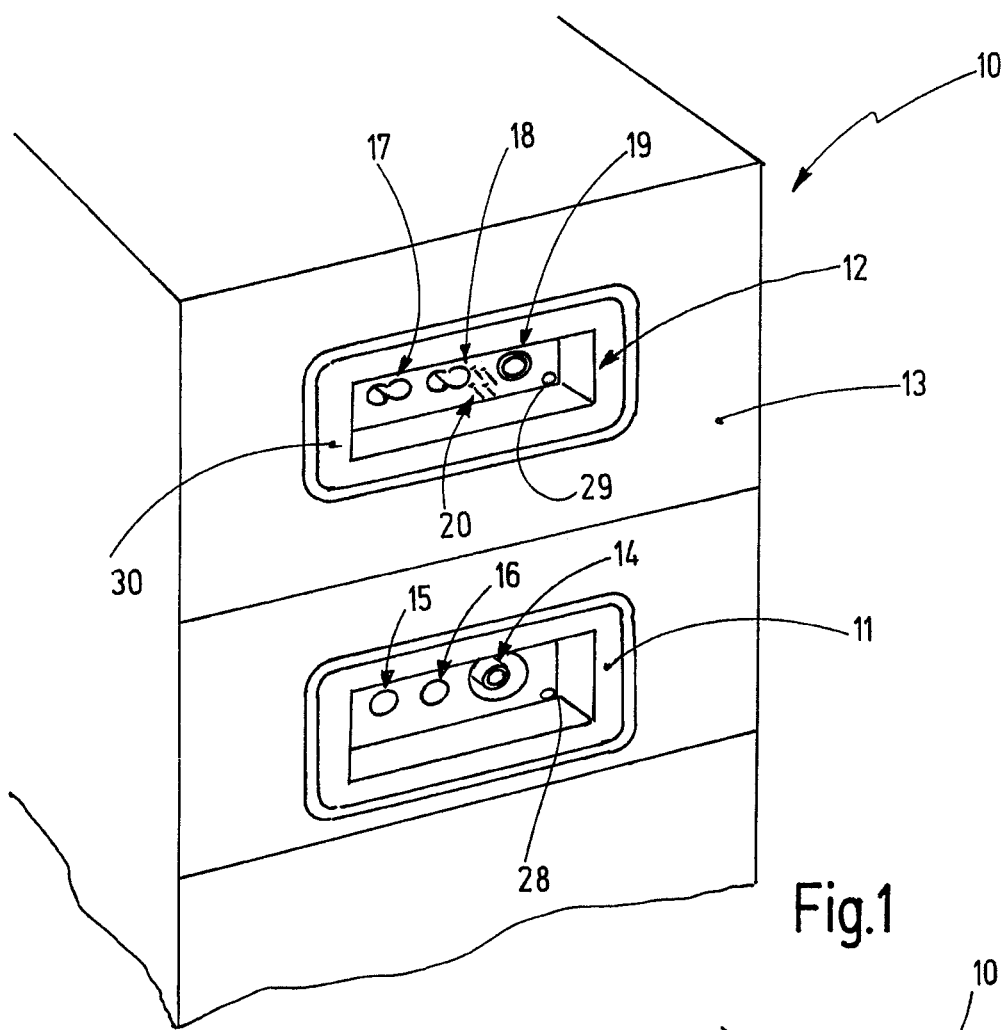
FIG. 1 an inventive apparatus in partially simplified perspective illustration with view toward its front side, FIG. 2 an apparatus according to FIG. 1 with a removed socket insert in a perspective illustration, FIG. 3 the socket insert for the apparatus according to FIGS. 1 and 2 in perspective illustration, FIG. 4 a service insert for the apparatus according to FIGS. 1 and 2, FIG. 5 the socket insert according to FIG. 3 in back view, FIG. 6 the service insert according to FIG. 4 in back view, FIG. 7 the apparatus of FIGS. 1 and 2 in a schematic block diagram illustration, FIG. 8 an alternative embodiment of the inventive apparatus in a schematic block diagram illustration.

FIG. 1 illustrates an apparatus 10 that serves for supply of one or more not illustrated instruments. The exemplarily shown apparatus 10 serves, for example, for supply of the respective medical instruments with operation media, as for example fluidic media, that is e.g. gases, aerosols and/or liquids. The expression "supply" also comprises the reception of media from the instrument, i.e. the provision of vacuum or suction power for suction purposes. Alternatively or additionally, the apparatus can be configured for supply of one or more medical instruments with electric current. Additionally or alternatively, the apparatus 10 can be configured for the supply of the medical instrument with light or also for reception of light that was received or created by the instrument. This also shall be understood by the expression of "supply of operating media".

For the supply of at least one operating medium, the apparatus 10 can provide one or more connection possibilities for medical instruments. In the apparatus exemplarily illustrated in FIG. 1 two connection possibilities are present provided by socket inserts 11, 12. These socket inserts 11, 12 are arranged at the front side 13 of the apparatus 10. The socket inserts 11, 12 are preferably configured such that they contain the necessary connections for operating an instrument. For example, the socket insert 11 comprises a socket 14 for a fluid and/or additional sockets 15, 16 for electric current. The sockets 15, 16 can conduct operating current, controlling current, e.g. in order to control the apparatus 10 by the connected instrument, or treatment currents, measurement currents and the like. The apparatus may (but not necessarily) comprise additional connections, e.g. one or more connections for a neutral electrode.

The socket insert 12 is exemplarily illustrated as exclusive electric socket that comprises multiple sockets 17, 18, 19 for the treatment current of an instrument to be connected. In addition, one or more pins 20 can be provided at the socket insert 12 that can serve to detect the type of inserted plug and that can be arranged axially immovably or axially movably. In addition one or more connections can be provided that are part of control lines and via which operating elements provided at the instrument are connectable with the apparatus control.

The socket inserts 11, 12 are only of exemplary kind. Also a socket insert can be provided that exclusively comprises one or more fluid sockets. A socket insert can be provided that exclusively comprises one or more connections for light in order to conduct light to the instrument or receive light therefrom. In addition, a socket insert can be provided that exclusively comprises one or more connections at which a suction function (vacuum) is provided. A socket insert can be provided that comprises at least one connection for treatment current, signal current or other carrier of energy and/or information. It is also possible to provide a socket insert that comprises two or more of the connections of different types mentioned above.

Figure 2:
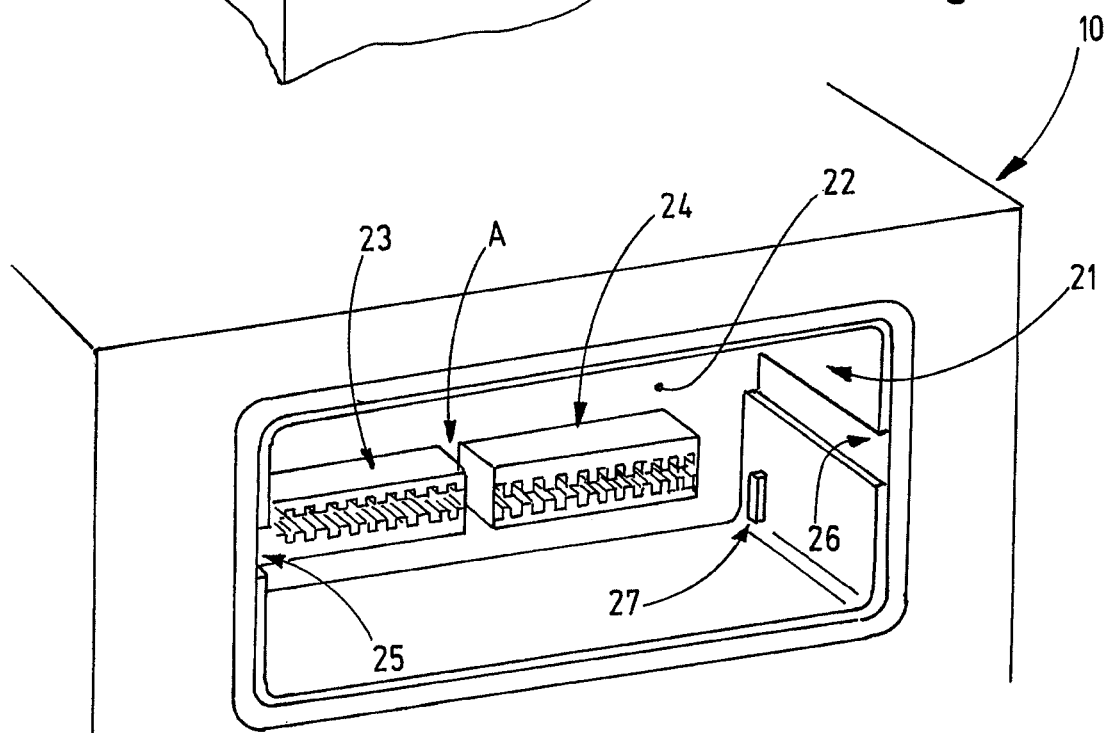

Each socket insert 11, 12 is arranged in a receptacle. FIG. 2 illustrates exemplarily a receptacle 21. The receptacle 21 comprises an operating medium output 23 and a data interface, e.g. in form of a data plug 24, at its back wall 22. The operating medium output 23 and the data plug 24 are arranged in sideward distance A that provides an electrical insulation between the operating medium output 23 and the data plug 24 and thus the necessary air and creeping distances.

The operating medium output 23 is illustrated as electrical plug with multiple contacts, wherein however the operating medium output shall not be considered to be limited to a plug of this type. The operating medium output 23 can be formed by any connection means that is suitable for safe transfer of the respective operating medium from the apparatus 10 to the socket insert 12 (or 11). The same applies for the data plug 24. In FIG. 2 also the data plug is illustrated as multiple pole socket. The data plug 24 can, however, also be any other connector suitable for data transmission.

As desired, guides 25, 26 for the socket insert 12 and/or latch projections 27 being part of a locking device or other latch means can be arranged in the receptacle 21 in order to lock the socket insert 11 or 12 in a manner that is, for example, illustrated in EP 2 904 982 A1. Respective release pins 28, 29 for releasing of respective locking can be provided in the socket inserts 11, 12 and can be accessible from the front side.

Figure 3:
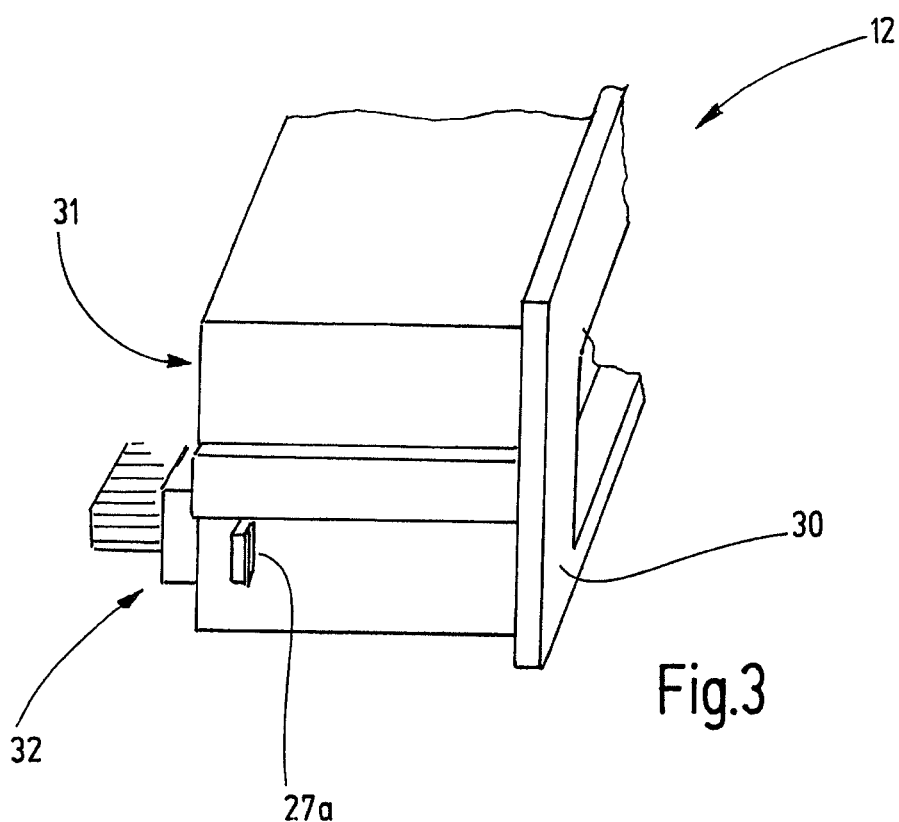

FIG. 3 illustrates the socket insert 12 separately in a sectional perspective illustration. At its back side 31 opposite the front side 30, an operating medium connector 32 is arranged that can be configured, for example, as plug matching the operating medium output 23. The operating medium connector 32 can comprise a number of electrical contacts that get in electrical conductance with the contacts of the operating medium output 23, if the socket insert 12 is completely inserted in the receptacle 21 and locked therein. The electrical contacts can be connected with contacts in the sockets 17, 18, 19 and/or with pins 20. If other operating media, such as fluid and/or light and/or vacuum, shall be conveyed, the socket insert has respective connectors at its back side 31 and at its front side 35.

Figure 5:
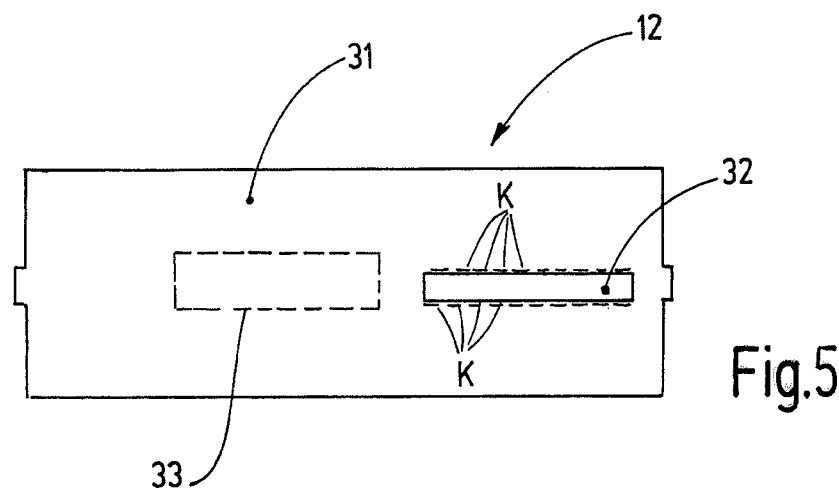

FIG. 5 illustrates the back side 31 of the socket insert 12 and the operating medium connector 32 with its contacts K in top view. As apparent, the operating medium connector 32 is spatially and functionally assigned to the operating medium output 23. Surface 33 opposed to the data plug 24 that is circumscribed in dashed lines in FIG. 5 for illustration purposes, is however empty.

During operation the socket insert 12 provides the operating currents and/or signal currents necessary for the connection of the instrument in the sockets 17, 18, 19 and, where appropriate, at pins 20. However, socket insert 12 covers the data plug 24 such that it remains inaccessible for the user of apparatus 10 and the user of the instrument. The apparatus 10 thus provides no possibility for the non-authorized and non-informed user to gain access intentionally or unintentionally to the data plug 24 and thus to the internal adjustment possibilities of the apparatus 10.

Figure 4:
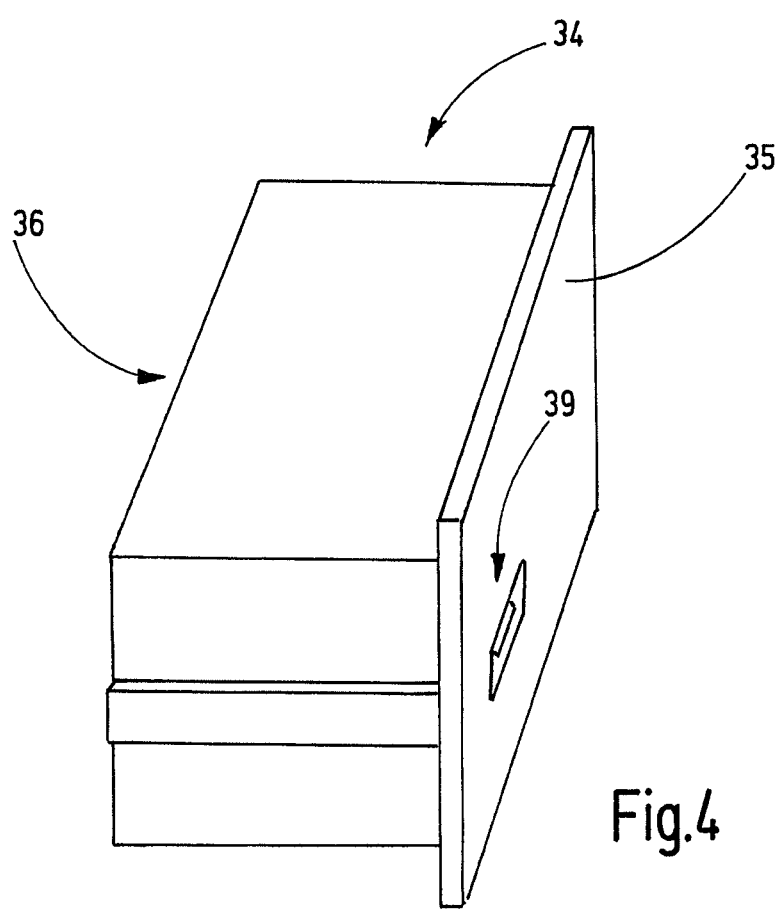
Figure 6:
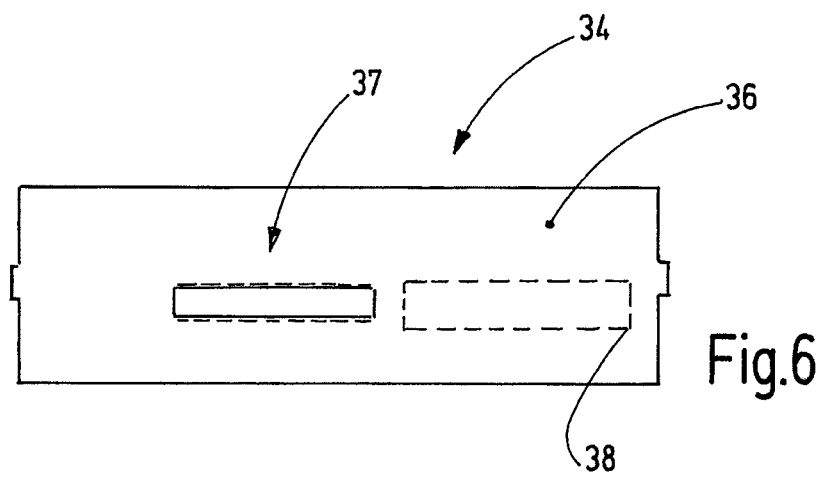

The service insert 34, as illustrated in FIGS. 4 and 6 is available for the service technician. It comprises an outer contour that is adapted to the inner contour of the receptacle 21 or is at least configured such that the insertion of the service insert 34 in the receptacle 21 is possible. The service insert 34 can thereby comprise such length that it ends with its front plate 35 flush with the front side 13 of the apparatus 10. Alternatively, the service insert 34 can, however, also be configured longer such that it extends out of the receptacle 21 after insertion. The service insert 34 can be provided with locking means as necessary, in order to lock it in the receptacle 21. Alternatively, such locking means can also be absent.

At its back side 36 facing away from the front plate 35 the service insert 34 comprises a data plug 37 (or another device that can be brought into connection with the data interface of apparatus 10), the form and position of which is adapted to the data plug 24 of the receptacle 21. The data plug 37 can be configured as multiple pole electrical plug that comprises a number of contacts that get in contact with the contacts of data plug 24, when the service insert 34 is inserted into the receptacle 21. The part 38 of the back side 36 that is thereby opposed to the operating medium output 23 is illustrated in FIG. 6 circumscribed by a dashed line. This area, i.e. this part 38 of the back side 36, is empty, i.e. no elements are arranged there that could get into electrical contact with contacts of the operating medium output 23.

The service insert 34 can be configured as passive element in the simplest case in that at its front plate 35 a socket 39 for connection of an electrical data processing device is provided. The contacts of socket 39 can be connected with respective contacts of the data plug 37. The socket 39 can be an arbitrary socket, e.g. a USB-socket, a network socket or the like.

The use and service of the apparatus 10 is as follows:

During normal operation the socket insert 12 is provided for the connection of an instrument and is operable. If apparatus 10 shall be made ready for operating other instruments, this can be facilitated by the service technician by exchange of the socket insert 12, in that this socket insert 12 is replaced by another suitable socket insert.

If the service technician, however, wants to update the software of apparatus 10, parameterize the apparatus 10 different from the present adjustments, read out operating data or measurement values from the apparatus 10 or input or output other data, he requires access to the service interface of the apparatus 10. This is formed by the data plug 24. For this purpose the service technician first removes socket insert 12 from the apparatus and now has access to the data plug 24. If it is configured as network socket or USB-socket (different to the illustration in FIG. 2), he can directly connect his laptop, notebook or other data processing device to this socket. However, preferably a data plug 24 is provided in the apparatus 10 that is not in conformity with the standards of a network socket or USB-socket, such that a non-authorized access to the apparatus software is further impeded. However, the service insert 34 is available to the service technician that he now inserts into the receptacle 21. If this has happened, it can connect a cable at the front plate 35 or the socket 39 respectively in order to establish a connection between its data processing device (laptop, notebook, etc.) and the control 40 of the apparatus 10 (see FIG. 7).

After the service has been carried out the service technician removes the service insert 34 from the receptacle 21 and inserts the socket insert 12 (or if an exchange is desired, another socket insert) into the receptacle 21.

Figure 7:
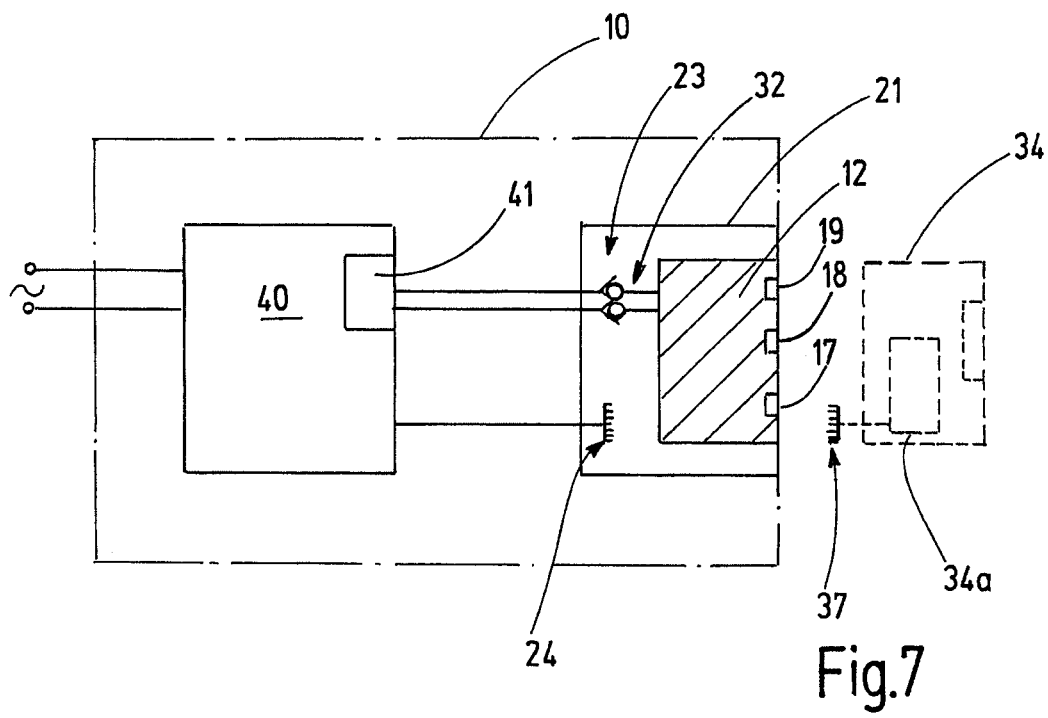
Figure 8:
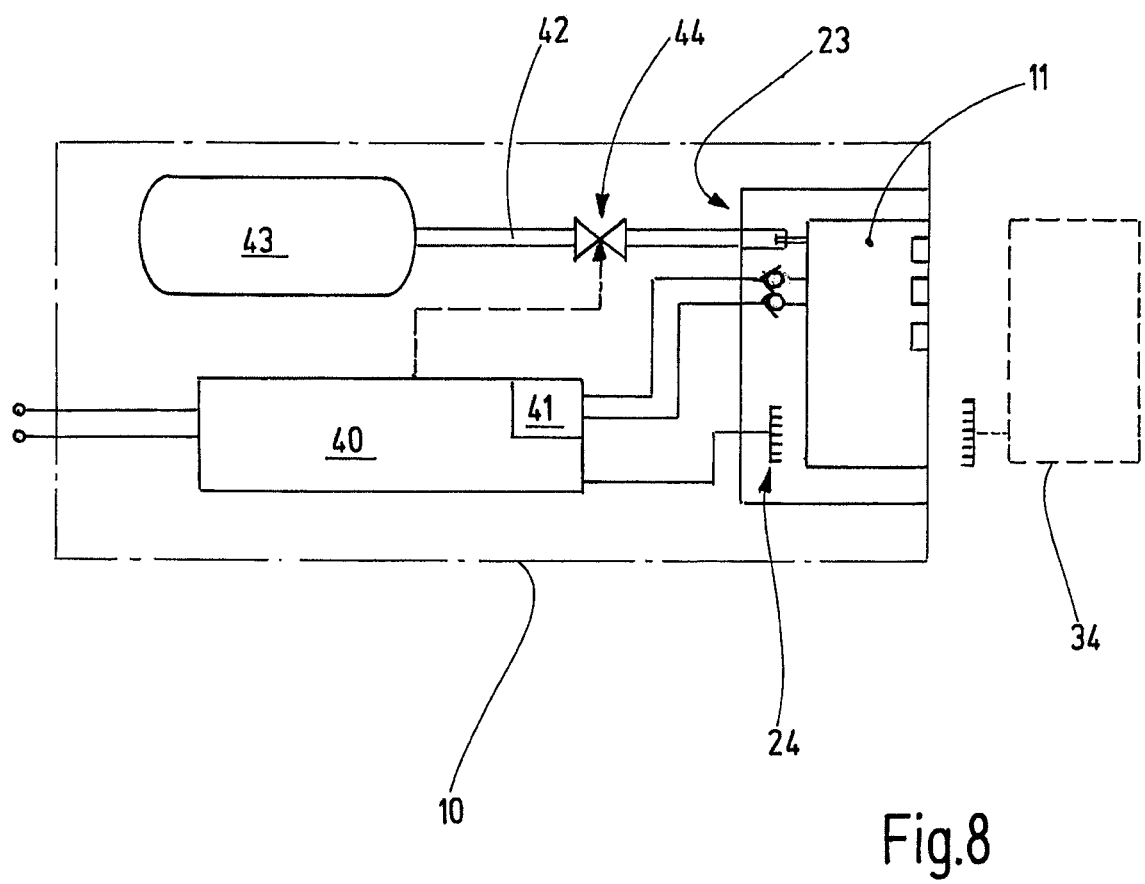

While FIG. 7 schematically shows an apparatus 10 with an electrical power section 41 that supplies the operating medium output 23, e.g. with radio frequency alternating voltage that is suitable for coagulation, ablation or dissection of biological tissue, FIG. 8 shows an apparatus 10, the control 40 of which in addition to this controls a fluid channel 42. This leads from a gas source 43 that can be configured as external gas source or also as illustrated within the apparatus 10, via at least one valve 44 to the operating medium output 23. Here, the operating medium output 23 comprises a plug for fluids as well as plugs for electrical voltage or the current respectively output from the power section 41.

Such a configuration can serve for supply of the socket insert 11, as illustrated in FIG. 4. Again, the socket insert 11 can be removed and replaced by the service insert 34 for service purposes that then provides access to the control 40 for the service technician.

Instead of a socket insert 11 that transmits fluidic media as well as current, also a socket insert 11 can be provided that only transmits fluidic media and/or other power or information-carrying media, as e.g. light. Also the fluid channel 42 can be configured as suction channel.

In all of the embodiments described above instead of a passive service insert 34, as illustrated in FIG. 4, a service insert can be provided that contains a storage medium and/or at least one information processing element itself, as for example, a microcontroller. Such a service insert 34 can be, for example, configured to bring in data or programs in the control 40 after the service insert 34 is inserted in the receptacle 21. In this case the front plate 35 can be, for example, configured without connection possibilities and plug possibilities for another computing device. Such a service insert 34 can be configured in addition or as an alternative to read out and store in itself data from control 40.

At such a service insert 34 also the socket illustrated in FIG. 4 can be provided in order to connect an external device, as e.g. a laptop or the like in order to control, to initiate or influence in another manner the data transmission from the service insert 34 to the control 40 or from control 40 to the service insert 34.

Also the service insert 34 can contain a radio transmission module, e.g. a Bluetooth module or a WLAN module in order to establish connection to an external data processing device, such as e.g. a mobile phone, a tablet, a notebook or a laptop, in order to allow communication between the control 40 and the respective mobile end device. In doing so, the service insert 34 can contain storage means and/or data processing means in addition to the radio transmission module.

The inventive apparatus 10 comprises a socket insert 11 that is arranged in a receptacle 21 of the apparatus 10. Thereby the socket insert 11 is connected to an operating medium connector 32 of the apparatus. In addition, in the receptacle 21 a data interface 24 is arranged that is covered by the socket insert 11 and thus inaccessible from outside.

In order to obtain access to the apparatus software and/or apparatus data, socket insert 11 can be removed and replaced by a service insert 34 that on one hand covers the operating medium output 23, but contacts the data plug 24. In this connection the service insert 34 can communicate directly or an external device (laptop, notebook, table, etc.) can communicate via the service insert 34 with the apparatus control 40 in order to input or output data and/or programs, as well as in order to update programs, change data, in order to change apparatus parameters or the like. The arrangement of the service interface covered by socket inserts 11, 12 provides an effective means for access control to the service interface. It impedes or avoids non-authorized access to the interface and damages for persons and material that otherwise could occur due to the missing disruptive discharge proof potential separation between the service interface and particularly the power section of the apparatus control.

LIST OF REFERENCE SIGNS 10 apparatus
11 socket insert
12 socket insert
13 front side
14 socket for fluid or for bipolar coaxial plug—depending on embodiment
15-19 socket for electric current
20 pins
21 receptacle
22 back side
23 operating medium output
14 data plug
A distance
25, 26 guides
27 latch projection
27a locking device
28, 29 release pins
30 front side
31 back side
32 operating medium connector
K contacts
33 free surface
34 service insert
35 front plate
36 back side
37 data plug
38 area
39 socket
40 controller
41 power section
42 fluid channel
43 gas source
44 valve

The invention claimed is:

1. An apparatus (10) for supply of medical instruments with operating media, comprising:
   a housing in which a controller (40) is arranged, the controller (40) configured to control an operation of the apparatus, the housing including at least one operating medium output (23), the housing further including at least one data plug (24) operably connected with the controller (40) configured for transmitting data to and/or from the controller (40),
   a receptacle (21) in which the at least one operating medium output (23) and the at least one data plug (24) are arranged, wherein the at least one operating medium output (23) and the at least one data plug (24) are separate and spaced apart from one another,
   a socket insert (11, 12) that is arranged in the receptacle (21) and configured to prevent access to and use of the at least one data plug (24) for transmitting data to and/or from the controller (40), wherein the socket insert (11, 12) comprises an operating medium connector (32) on an apparatus side of the socket insert that is releasably connected with the at least one operating medium output (23), the socket insert further including an instrument connection (14-19) accessible from outside that is connected with the operating medium connector (32), wherein the socket insert lacks a data plug connector for being operably connected to the at least one data plug (24) on the apparatus side of the socket insert.

2. The apparatus according to claim 1, wherein the socket insert (11, 12) is not operably connected with the at least one data plug (24).

3. The apparatus according to claim 1, wherein the socket insert (11, 12) includes a locking device (27a) for locking of the socket insert (11, 12) in the receptacle (21).

4. The apparatus according to claim 1, wherein the socket insert (11, 12) has a contour adapted to fit a corresponding contour of the receptacle (21).

5. A service insert (34) for an apparatus (10) according to claim 1, comprising:
   a housing that comprises a data plug (37) at an end face (36) of the housing that is adapted to be operably engaged with the at least one data plug (24) of the apparatus (10).

6. The service insert according to claim 5, wherein the service insert comprises a contour adapted to fit a corresponding contour of the receptacle (21).

7. The service insert according to claim 5, wherein the service insert (34) is free of a connection configured to connect with the at least one operating medium output (23).

8. The service insert according to claim 5, further comprising a storage medium (34*a*) that is operably connected with the data plug (37).

9. The service insert according to claim 5, further comprising an interface (39) configured for communication with a computer.

10. The service insert according to claim 9, wherein the interface (39) is a USB-interface.

11. The service insert according to claim 9, wherein the interface (39) is a network interface.

12. The service insert according to claim 9, wherein the interface is a radio connection.

13. A method for servicing an apparatus according to claim 1, comprising the following steps:
   removing the socket insert (11, 12) from the receptacle (21),
   inserting a service insert (34) having a housing that comprises a data plug (37) at an end face (36) of the housing that is adapted to be operably engaged with the at least one data plug (24) of the apparatus (10), in the receptacle (21),
   activating the service insert (34),
   removing the service insert (34) from the receptacle (21),
   inserting the socket insert (11, 12) in the receptacle (21).

\* \* \* \* \*